United States Patent [19]

Tosa et al.

[11] Patent Number: 4,691,054

[45] Date of Patent: Sep. 1, 1987

[54] METHOD FOR SEPARATING A BASIC AMINO ACID

[75] Inventors: Takafumi Tosa, Kawasaki; Yoshihiro Koga; Tsutomu Matsuishi, both of Saga, all of Japan

[73] Assignee: Ajinomoto Co., Inc., Tokyo, Japan

[21] Appl. No.: 905,126

[22] Filed: Sep. 9, 1986

[30] Foreign Application Priority Data

Sep. 13, 1985 [JP] Japan .................................. 60-202702

[51] Int. Cl.$^4$ .............................................. C07C 99/12
[52] U.S. Cl. .................................................. 562/554
[58] Field of Search ........................................ 562/554

[56] References Cited

U.S. PATENT DOCUMENTS

| | | | |
|---|---|---|---|
| 2,462,597 | 2/1949 | Block | 562/554 |
| 3,505,399 | 4/1970 | Samejima | 562/554 |
| 3,686,118 | 8/1972 | Benson | 562/554 |

FOREIGN PATENT DOCUMENTS

| | | | |
|---|---|---|---|
| 1074049 | 8/1956 | Fed. Rep. of Germany | 562/554 |
| 49-34906 | 9/1974 | Japan | 562/554 |
| 53-84914 | 7/1978 | Japan | 562/554 |
| 56-65849 | 6/1981 | Japan | 562/554 |

Primary Examiner—Michael L. Shippen
Attorney, Agent, or Firm—Oblon, Fisher, Spivak, McClelland & Maier

[57] ABSTRACT

A method for separating a basic amino acid from a liquor containing the same, which entails (a) contacting the basic amino containing liquor with a strongly acidic cation exchange resin at a pH at which the basic amino acid exists in the form of a divalent cation, thereby adsorbing at least a part of the basic amino acid in the form of the divalent cation; (b) contacting said ion exchange resin with a liquor containing said basic amino acid and a neutral amino acid or an acidic amino acid at a pH at which the basic amino acid exists in the form of a monovalent cation; (c) passing an eluant through said ion exchange resin, thereby eluting the basic amino acid from the ion exchange resin; and (d) separating and recovering the basic amino acid from the eluate.

8 Claims, No Drawings

METHOD FOR SEPARATING A BASIC AMINO ACID

BACKGROUND OF THE INVENTION

1. Field of the Invention

This invention relates to a method for separating a basic amino acid from a fermentation liquor, for example.

2. Description of the Background

Basic amino acids are conventionally obtained by separation from amino acid mixtures obtained by decomposing proteins. Currently basic amino acids are produced mainly by fermentation processes. However, in fermentation processes, neutral and acidic amino acids are producted as by-products and the removal of these neutral and acidic amino acids is always a significant problem. At present, the separation and/or removal of these by-product amino acids is generally effected by using a strongly acidic cation exchange resin.

Unfortunately, when using the ion exchange resin method, it is necessary to balance the yield of the basic amino acid and the rate of removal of the neutral and acidic amino acids. However, in industrial production, since reductions in the yield of the basic amino acid are to be avoided, much less of the neutral and acidic amino acids is removed than is desirable. Consequently, the ion exchange resin treated liquor is invariably and inevitably contaminated with such neutral and acidic amino acids. Unfortunately, these amino acids are a frequent cause of difficulty in recovering basic amino acid crystals from the ion exchange resin treated liquor.

Hence, a need clearly continues to exist for a method by which basic amino acids can be separated from a liquor containing the same and from neutral and acidic amino acids also contained therein, without compromising the yield of the basic amino acid.

SUMMARY OF THE INVENTION

Accordingly, it is an object of this invention to provide a method for separating a basic amino acid from a liquor containing basic, neutral or acidic amino acids, or a mixture thereof.

It is also an object of the present invention to provide such a method whereby the neutral and acidic amino acids are also separated and eliminated.

According to the present invention, these objects and others which will become more apparent are accomplished by providing a method for separating a basic amino acid from a liquor containing the same, which entails contacting said liquor with a strongly acidic cation exchange resin at a pH in which said basic amino acid is capable of existing in the form of a divalent cation, thereby adsorbing at least a part of the basic amino acid in the form a divalent cation; thereafter contacting said ion exchange resin with a liquor containing the basic amino acid and a neutral amino acid or an acidic amino acid or a mixture thereof, at a pH at which the basic amino acid is capable of existing in the form of a monovalent cation; and then passing an eluant through the ion exchange resin to elute the basic amino acid; and separating and recovering the basic amino acid from the eluate.

DETAILED DESCRIPTION OF THE PREFERERED EMBODIMENTS

According to the present invention, the basic amino acid containing liquor is a liquor containing lysine, arginine, ornithine, or histidine, for example. Examples of such liquors include fermentation liquors of these amino acids, intermediate process liquors from which these basic amino acids are separated, hydrolysate liquors of proteins such as soybean protein etc., and intermediate process liquors from which these basic amino acids are separated, for example. Examples of the intermediate liquors from which the basic amino acids are separated include sterilized fermentation liquors, crude crystal dissolved liquors, and crystallization mother liquors, for example.

The strongly acidic cation exchange resin may be any of the conventional commercially available products, for example, Dowex HCR-W2, Duolite C-20, Diaion SK-1B, Amberlite IR-120 (Trade names). The resins may be in the form of a salt such as $NH_4$, or Na etc., or may be in a free form.

The adsorption is effected by contacting the basic amino acid containing liquor with a strongly acidic cation exchange resin at a pH at which the basic amino acid can exist in the form of a divalent cation. This pH varies depending on the kind of the basic amino acid, but generally not higher than about 4.0. In the case of lysine, it is not higher than pH 4.0. A pH of about 1–2.5 is particularly preferred in view of the amount adsorbed. Where a salt form ion exchange resin is used, the starting liquor may be adjusted to such a pH and supplied to the ion exchange resin layer, whereas if an ion exchange resin layer containing a free form is passed through, the optimum pH for the starting liquor is higher because hydrogen ions are released by the adsorption. Where the ion exchange resin is completely in the free form, for example, the optimum pH for a lysine fermentation liquor is about pH 4–6.

The ion exchange resin to which the basic amino acid has been adsorbed is then contacted with a liquor containing said basic amino acid and a neutral amino acid or an acidic amino acid or both at a pH at which the basic amino acid does not exist in the form of a divalent cation but can exist in the form of a monovalent cation. The neutral amino acid and the acidic amino acid are those constituting proteins, and they are, for example, glycine, alanine, valine, threonine, glutamic acid, and aspartic acid, for example. Inorganic ions such as ammonium, sodium, potassium, calcium, magnesium etc. elute the adsorbed basic amino acid, and therefore, it is preferable that they are not present. Examples of such a liquor include a liquor fraction in which a neutral amino acid and an acidic amino acid have been eluted and which has been obtained by passing a basic amino acid fermentation liquor or an intermediate process liquor from which the basic amino acid is separated through a strongly acidic cation exchange resin layer to adsorb said basic amino acid and thereafter passing an alkali through said ion exchange resin layer, and a crystallization method liquor substantially not containing the aforesaid inorganic ions. In this case, the liquor fraction in which the neutral amino acid and the acidic amino acid have been eluted may be separated and recovered by using, for example, the pH, specific gravity, or refractive index as an index, but since the value of this index on separating and recovering varies depending on the nature of the starting liquor, among other factors, it is necessary to determine this value initially by experimentation. It is not necessary to delay separation and recovery of the basic amino acid until the neutral and acidic amino acids have been completely eluted. In fact, migration thereof to an extent which does not adversely affect the subsequent steps may be tolerated. Using ammonia water alone or further containing an ammonium salt as an eluant is concentrated to evaporate the ammonia. Then, after adjusting the pH by adding an acid if necessary, concentrated, cooled and crystallized by e.g. adding an organic solvent to obtain a mother liquor, which is in general the crystallization mother liquor substantially free of inorganic ions.

The pH at which the basic amino acid can exist in the form of a monovalent cation rather than the divalent cation varies depending on the kind of the basic amino acid, and, for example, in the case of lysine, it is a pH of about 4.0–10.0. This is a generally applicable pH range. By utilizing such a pH, the basic amino acid adsorbed as a divalent cation is converted to a monovalent cation, and a result, the ion exchange resin becomes able to adsorb the basic amino acid afresh. On the other hand, in such a pH region, since the neutral and acidic amino acids exist exclusively in the neutral form or the anionic form, they cannot be adsorbed to the strongly acidic cation exchange resin. Further, since the neutral and acidic amino acids which have been already adsorbed to the ion exchange resin also pass from the ion exchange resin, the amino acids which are adsorbed to the ion exchange resin at the end of this step are mainly composed of the basic amino acid. Of course, the amount of the eluant to be passed should be in the range within which the basic amino acid does not break through. Where a liquor containing an inorganic ion is used, the basic amino acid tends to break through and therefore the amount of the eluant which can be safely passed is greatly reduced.

A conventional eluant may be used as such, and, for example, ammonia water, an aqueous sodium hydroxide solution or these solutions but further containing ammonium chloride, sodium chloride etc. are used at concentrations of about 0.5–5 N.

The separation of the basic amino acid from the eluate may be effected in a conventional manner. For example, where ammonia water is used as the eluant, the ammonia is evaporated by concentration, then, the pH is adjusted by adding a hydrochloric acid if necessary, followed by further concentration and subsequent cooling to induce crystallization, thereby crystals may be obtained.

In the method of this invention, since the basic amino acid purity of the eluate is high, the growth of crystals in the subsequent crystallization step is good, and moreover, crystals of a high purity may be easily obtained. Moreover, since the concentration of the basic amino acid of the eluate is increased, the energy required for concentrating the same is decreased. In particular, where the continuous-column adsorption and the continuous-column elution were effected by using a basic amino acid fermentation liquor as a starting material and employing a plurality of ion exchange resin columns, the eluate fraction of the neutral and acidic amino acids may be easily incorporated in continuous operations.

In order to illustrate the present invention, various examples will now be provided which are added only for purposes of illustation and are not intended to limit the present invention in any manner.

EXAMPLE 1

A lysine fermentation liquor mainly starting from beet molasses was used as a sample liquor after removing the microbial cells and adjusting to pH 2. The lysine content in the sample liquor was 5.0 g/dl calculated as the lysine hydrochloride (hereinafter the lysine amount is calculated as the lysine hydrochloride amount).

Resin operations were conducted by connecting two columns, each packed with one liter of an $NH_4+$ form of Diaion SK-IB in series and passing 2 l of the sample liquor from the top of the first column at a rate of 20 ml per minute. Thereafter, washing with 1.5 l of pure water was conducted from the first column. Further, the first column was disconnected, and a third columm was connected to the second column, and similar operations were conducted.

The first column was passed and eluted with 2 l of 2 N ammonia at a rate of 20 ml per minute, and further washed with 2 l of pure water. The fraction of the eluate having a lysine concentration of 8 g/dl or higher was collected, and the eluate having a lesser concentration was passed through the second column, which was then washed with 1.5 l of pure water.

Ten cycles of similar resin operations were repeated.

In order to confirm the effect of this invention, as a comparison, a conventional resin operating method, i.e., resin operating method in which the eluate was all collected and was not recycled to the adsorption step was experiemtned for 10 cycles. The tail port of the eluate which had a sugar value of 1 or less was excluded.

The properties of the collected eluates in the 10th cycle are shown in Table I (the nitrogen purity is the proportion of the lysine-derived nitrogen in the organic nitrogen determined by the elemental analysis).

TABLE I

| Treating Method | Nitrogen Purity (%) | Lysine Concentration (g/dl) |
|---|---|---|
| Present Method | 97.1 | 11.6 |
| Conventional Method | 86.1 | 6.0 |

The yield of the lysine in the resin step was about 98% in either method.

EXAMPLE 2

An arginine fermentation liquor mainly starting from cane molasses was used as a sample liquor after removing the microbial cells and adjusting to pH 2. The arginine content in the sample liquor was 4.0 g/dl. Thereafter, treatment was conducted in a manner similar to that in Example 1 except that the amount of the sample liquor in Example 1 was changed from 2 l to 3 l, the amount of the 2 l of the 2 N ammonia was changed to 6 l of 1 N ammonia, and that the arginine concentration to be collected was changed to 2.5 g/dl or higher. The properties of the collected eluates in the 10th cycle are shown in Table II (the nitrogen purity is that proportion of the arginine-derived nitrogen in the organic nitrogen determined by the elemental analysis).

TABLE II

| Treating Method | Nitrogen Purity (%) | Arginine Concentration (g/dl) |
|---|---|---|
| Present Method | 85.0 | 4.4 |

TABLE II-continued

| Treating Method | Nitrogen Purity (%) | Arginine Concentration (g/dl) |
| --- | --- | --- |
| Conventional Method | 83.0 | 3.5 |

The yield of the arginine in the resin step was about 94% in either method.

EXAMPLE 3

The eluate of the conventional method in Example 1 was collected, concentrated, then adjusted to pH 5 by adding hydrochloric acid, further concentrated, cooled, and the crystals were separated to prepare a mother liquor. The rate of crystallization was about 50%. The mother liquor had a lysine concentration of 34.2 g/dl and a nitrogen purity of 72.1%.

Two 4-liter portions of the same sample liquor as in Example 1 were passed through two columns, each packed with one liter of an $NH_4+$ form of Diaion SK-1B, respectively at a rate of 40 ml per minute, and thereafter washed with 1.5 l of pure water respectively.

One resin was left as such and the other resin was passed through with a 5-fold dilution of the mother liquor, washed with one liter of pure water, then eluted with 2 l of 2 N ammonia and washed with 2 l of pure water.

The tail part of each eluate which had a sugar value of 1 or less was excluded.

The results are shown in Table III.

TABLE III

| Treating Method | Nitrogen Purity (%) | Lysine Concentration (g/dl) | Amount of the Lysine Resin Adsorbed (g/l-R) |
| --- | --- | --- | --- |
| Method of the Invention | 95.5 | 7.9 | 146 |
| Conventional Method | 90.3 | 7.0 | 123 |

Having now fully described the present invention, it will be apparent to one skilled in the art that many variations and modifications can be made hereto without departing from the spirit and the scope of the present invention.

The strongly acidic cation exchange resins of the present invention include the styrene base sulfonic cation exchange resins, of which some examples are Dowex HCR-W2, Duolite C-20, Diaion SK-1B and Amberlite IR-120.

What is claimed as new and is intended to be secured by Letters Patent is:

1. A method for separating a basic amino acid from a liquor containing the safe, which comprises:
   (a) contacting the basic amino acid containing liquor with a strongly acidic cation exchange resin at a pH at which the basic amino acid exists in the form of a divalent cation, thereby adsorbing at least a part of the basic amino acid in the form of the divalent cation;
   (b) contacting said ion exchange resin with a liquor containing said basic amino acid and a neutral amino acid or an acidic amino acid or both at a pH at which the basic amino acid exists in the form of a monovalent cation;
   (c) passing an eluant through said ion exchange resin, thereby eluting the basic amino acid from the ion exchange resin; and
   (d) separating and recovering the basic amino acid from the eluate.

2. The method according to claim 1, wherein said basic amino acid containing liquor is a basic amino acid fermentation liquor or an intermediate process liquor from which the basic amino acid is separated, and the liquor containing said basic amino acid and said neutral amino acid or said acidic amino acid, or both, is substantially free of inorganic cations.

3. The method according to claim 2, wherein the liquor containing said amino acid and said netural amino acid or said acidic amino acid, or both, which is substantially free of inorganic cations is either a liquor fraction in which the neutral amino acid and the acidic amino acid have been eluted and which has been obtained by passing a basic amino acid fermentation liquor or an intermediate process liquor from which the basic amino acid is separated through a strongly acidic cation exchange resin layer to adsorb said basic amino acid and thereafter passing an alkali through said ion exchange resin layer, or a crystallization mother liquor substantially not containing an inorganic cation.

4. The method according to claim 1, wherein said basic amino acid containing liquor is contacted with the acidic cation exchange resin at a pH of not higher than about 4.0.

5. The method according to claim 4, wherein said basic amino acid containing liquor is contacted with the acidic cation exchange resin at a pH in the range of about 1-2.5.

6. The method according to claim 1, wherein said liquor containing the basic amino acid and the neutral or acidic or both amino acids is contacted with the acidic cation exchange resin at a pH in the range of about 4.0-10.0.

7. The method according to claim 1, wherein said eluant is ammonia water or an aqueous sodium hydroxide solution having a concentration in the range of 0.5-5.0 N.

8. The method according to claim 7, wherein said eluant further contains ammonium chloride or sodium chloride.

* * * * *

UNITED STATES PATENT AND TRADEMARK OFFICE
CERTIFICATE OF CORRECTION

PATENT NO. : 4,691,054
DATED : September 1, 1987
INVENTOR(S) : Tosa et al

It is certified that error appears in the above-identified patent and that said Letters Patent is hereby corrected as shown below:

| Col. | Line | |
|---|---|---|
| ABSTRACT | 3 | delete "amino containing" and insert --amino acid containing--, |
| 1 | 17 | delete "producted" and insert --produced--, |
| 2 | 2 | delete "PREFERERED" and insert --PREFERRED--, |
| 3 | 21 | delete "and a result" and insert --and as a result--, |
| 4 | 15 | delete "third columm" and insert --third column--, |
|   | 31 | delete "experiemtned" and insert --experimented--, |
| 5 | 54 | delete "safe," and insert --same,--, |

Signed and Sealed this

Seventeenth Day of May, 1988

Attest:

DONALD J. QUIGG

*Attesting Officer*

*Commissioner of Patents and Trademarks*